Figure 4:
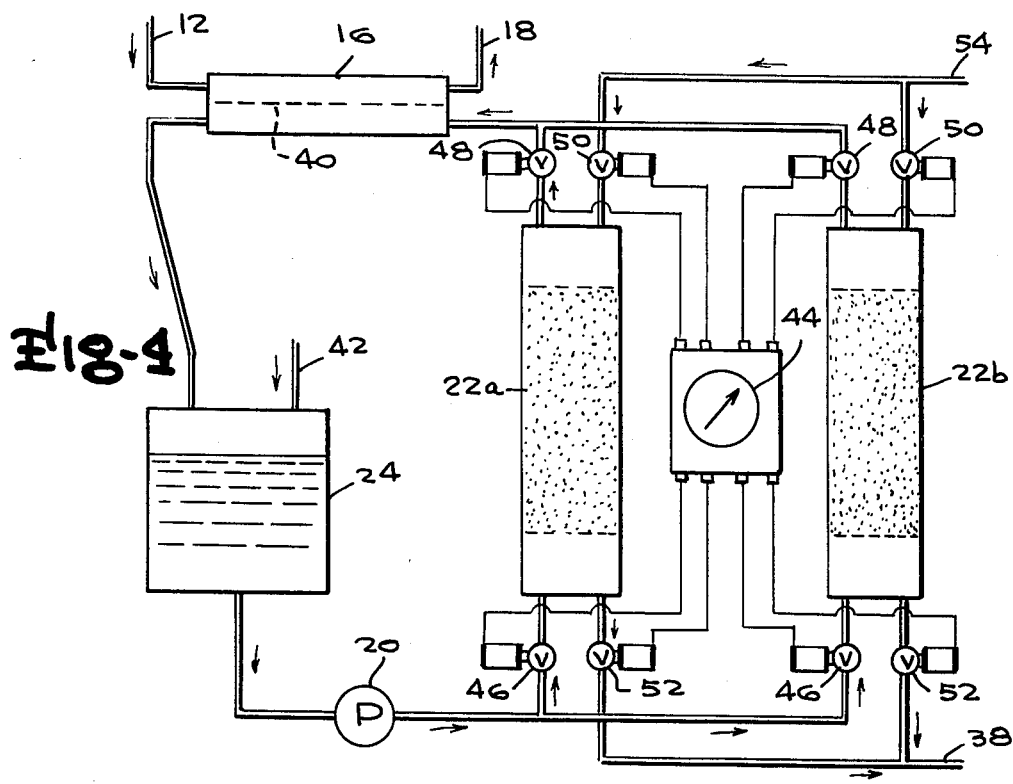

United States Patent [19]
Yoshida

[11] 4,118,314
[45] Oct. 3, 1978

[54] APPARATUS FOR TREATMENT OF ARTIFICIAL KIDNEY DIALYZING FLUID

[75] Inventor: Fumitake Yoshida, Kyoto, Japan

[73] Assignee: Seisan Kaihatsu Kagaku Kenkyusho, Kyoto, Japan

[21] Appl. No.: 578,939

[22] Filed: May 19, 1975

Related U.S. Application Data

[63] Continuation of Ser. No. 432,092, Jan. 9, 1974, abandoned.

[51] Int. Cl.² ............. B01D 13/00; B01D 15/06
[52] U.S. Cl. .................. 210/22 C; 210/140; 210/321 B
[58] Field of Search ........... 210/22, 96 M, 321 B, 210/140

[56] References Cited
U.S. PATENT DOCUMENTS

| | | | |
|---|---|---|---|
| 3,441,136 | 4/1969 | Serfass et al. | 210/96 M |
| 3,578,167 | 5/1971 | Clack et al. | 210/140 X |
| 3,697,418 | 10/1972 | Johnson | 210/22 |
| 3,753,493 | 8/1973 | Mellor | 210/140 |

OTHER PUBLICATIONS

"Cyclic Adsorption of Urea from Artificial Kidney Dialyzing Fluid," Blaney, T. L. et al., Chemical Eng. Prog. Symposium Series, No. 84, vol. 64, pp. 112-119.

Primary Examiner—Charles N. Hart
Assistant Examiner—David R. Sadowski
Attorney, Agent, or Firm—Francis A. Keegan

[57] ABSTRACT

Apparatus for the treatment of dialysate for the hemodialyzer in which apparatus the dialysate is recirculated and urea and other toxins in the dialysate are removed by repeated adsorption on and desorption from an adsorbent packed in a plurality of adsorbent beds that are used alternately or in rotation. Valves controlling flows of recirculating dialysate and the liquid (water and fresh dialysate) for desorption to and from said adsorbent beds are operated automatically with use of a timing device.

6 Claims, 5 Drawing Figures

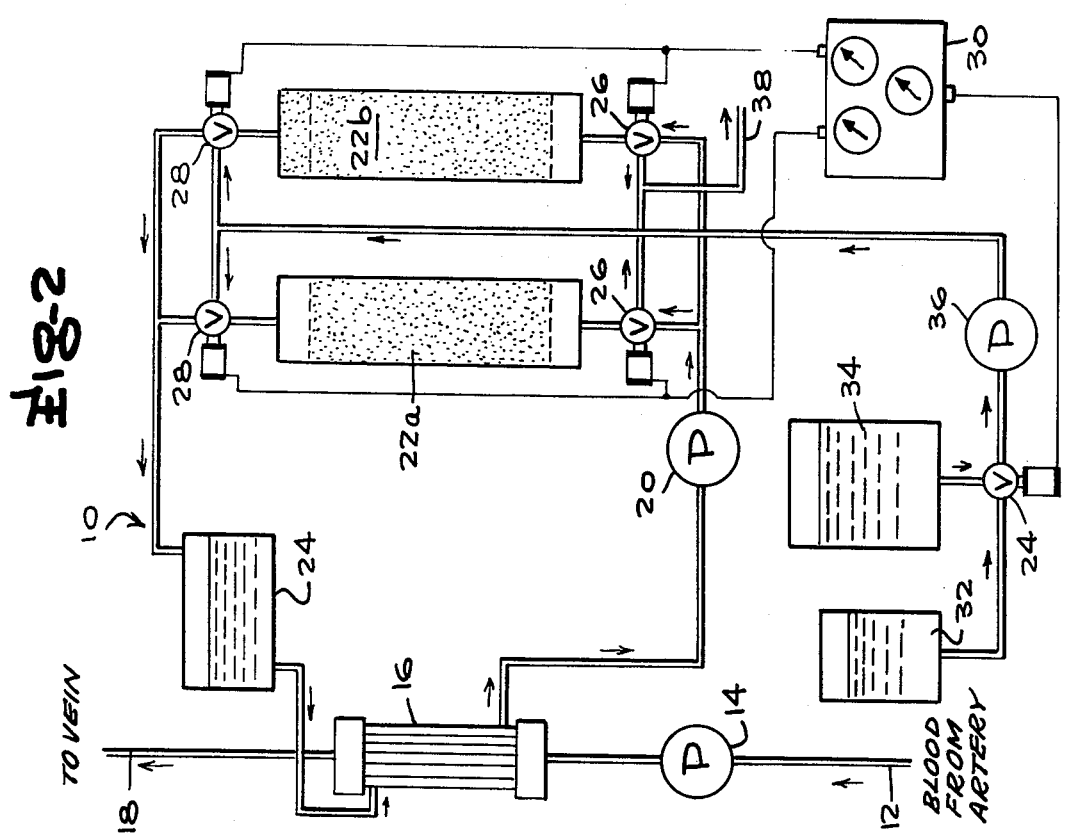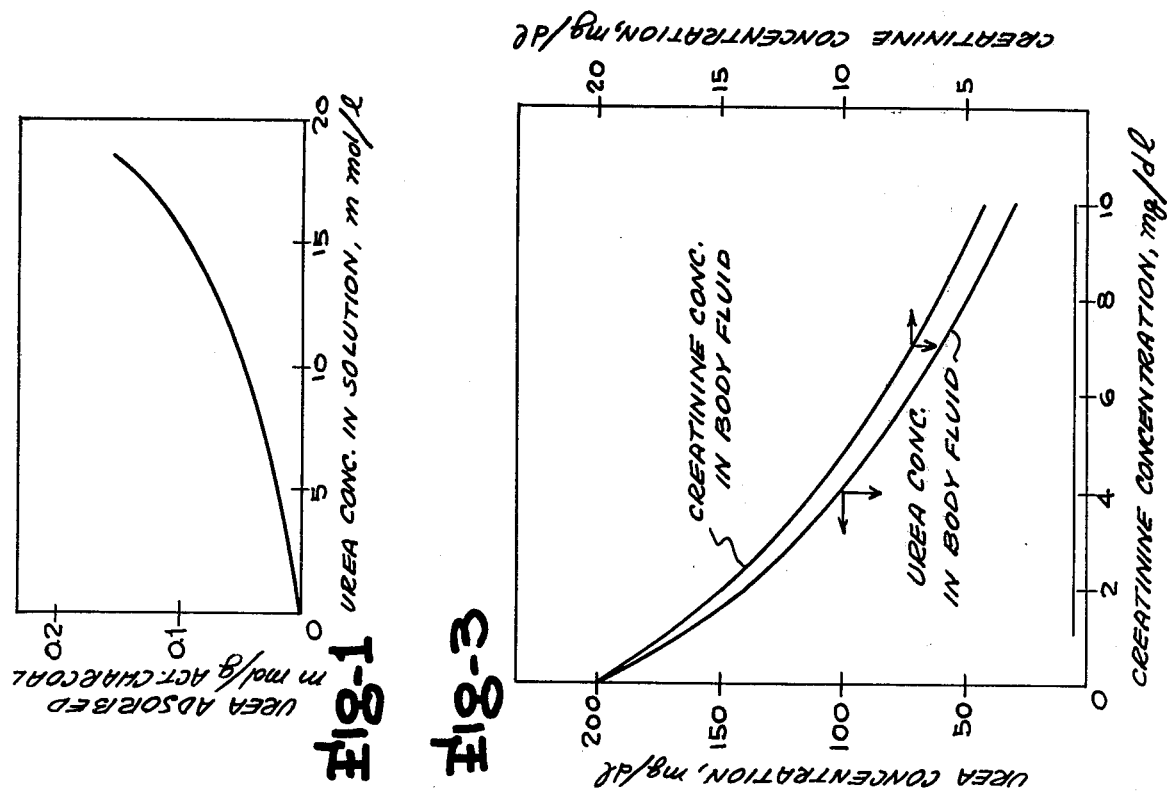

APPARATUS FOR TREATMENT OF ARTIFICIAL KIDNEY DIALYZING FLUID

This is a continuation of application Ser. No. 432,092, filed 1/9/74, now abandoned.

BACKGROUND OF THE INVENTION

This invention relates to an apparatus for removing urea and other toxins in the dialysate (dialyzing fluid) used for artificial kidneys otherwise referred to as hemodialyzers.

The artificial kidney is an apparatus for removing toxins (toxic waste metabolites) such as urea, creatinine, and uric acid from the blood of the patient of chronic uremia. In the hemodialyzing system, which is the most commonly used type of the artificial kidney, the blood from the artery of the patient is passed through a hemodizlyzer and is returned to the vein. The dialysate flows through the hemodialyzer and with the dialysate being separated from the blood by a conventional membrane such as cellophane, urea and other toxins in the blood are transferred into the dialysate by dialysis, that is, diffusion through the membrane.

The dialysate is an aqueous solution of various salts, glucose, and others, having an osmotic pressure approximately equal to that of blood. Since the driving potential for dialysis is the difference in concentration of urea and other toxins across the membrane, the rate of dialysis per unit area of the membrane in a given hemodialyzer varies in proportion to these concentration differences under given operating conditions such as blood and dialysate flow rates.

In a batch system with a dialysate tank, within which a certain amount of dialysate is recirculated, the rate of dialysis decreases as time goes on because the concentrations of urea etc. in the dialysate increase and consequently also the differences in the concentrations of toxins across the membrane decrease with time. In the conventional flow system, which is commonly adopted to avoid such increase in the concentrations of urea etc. in the dialysate with time, a fresh dialysate which does not contain urea etc. is continuously supplied to the hemodialyzer, and the dialysate leaving the hemodialyzer which contains urea etc. is discarded. However, this type of flow system requires a large quantity of dialysate, because hemodialysis usually must be conducted for as long as 8 to 12 hours. For example, if hemodialysis lasts 10 hours with a blood flow rate of 200 ml per minute and a dialysate flow rate of 500 ml per minute, the total amount of dialysate required will be 300 liters.

A batch system in which dialysate is recirculated within a tank would also require a large amount of dialysate if the increase in the concentrations of urea etc. in the dialysate is to be minimized. Thus, the cost of the dialysate is substantial. Also, it is not desirable to store such a large amount of prepared dialysate because of possible risk of bacterial contamination.

A commonly adopted procedure is to prepare dialysate by continuous dilution of a dialysate concentrate having a concentration approximately 35 times that of the dialysate, using tap water. However, such a continuous dilution system requires various complicated, expensive components including a proportioning pump. One of the reasons for the high cost of the conventional artificial kidney device is the use of such an expensive system for the continuous dilution of dialysate concentrate in the preparation of dialysate.

To solve this problem of the artificial kidney system requiring a large quantity of dialysate, it would be possible to remove urea etc. by appropriate means from the dialysate which is recirculated through a means in which urea etc. are removed. However, there has been no efficient system for such procedure. It is relatively easy to remove uric acid and creatinine from the dialysate by adsorption on an adsorbent such as activated charcoal or alumina. However, since any adsorbent adsorbs only a relatively small amount of urea due to the unfavorable equilibrium relationship for activated charcoal, a batch adsorption system requires a large amount of adsorbent. Also, it is inevitable in such a batch adsorption system that urea remains in the dialysate at a substantial concentration.

To remedy this shortcoming, Blaney et al. (Chemical Engineering Progress Symposium Series, No. 84, Vol. 4, p. 112-120 (1968)) proposed a system in which the dialysate is passed through a single bed of adsorbent which adsorbs toxins in the dialysate. After adsorption is completed, the toxins are desorbed from the adsorbent by passing water through the absorbent bed. This type of system in which a single bed of adsorbent is used to adsorb and desorb toxins in the dialysate in inefficient for the reasons mentioned subsequently and requires a relatively large amount of adsorbent.

It is accordingly an object of the present invention to provide an efficient and effective artificial kidney system using a recirculated dialysate and a plurality of adsorbent beds that permit substantially continuous adsorption and continuous desorption.

This and other objects of the present invention may be readily apparent from a perusal of the following description including the drawings.

DRAWINGS

FIG. 1 — Equilibrium diagram for urea adsorption on activated carbon.

FIG. 2 — Schematic drawing of the preferred embodiment of the present invention.

FIG. 3 — Diagram of plot of concentration of urea and creatinine in body fluid against dialysis time.

FIG. 4 — Schematic drawing of an alternate embodiment of the present invention.

Figure 5:
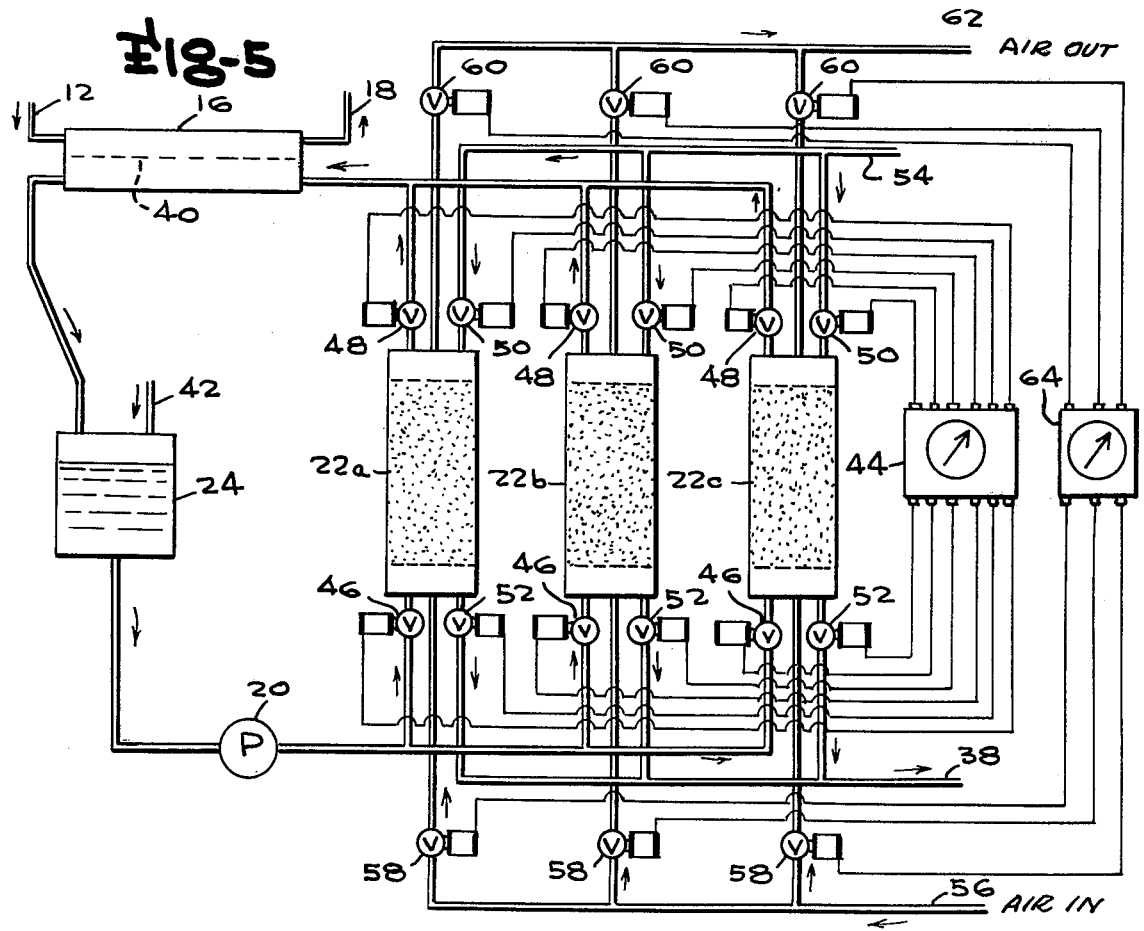

FIG. 5 — Schematic drawing of an alternate embodiment of the present invention.

SUMMARY OF THE INVENTION

In the apparatus of the present invention a plurality of adsorbent beds are used alternately or in rotation. The flows of the recirculating dialysate and the water and fresh dialysate used for desorption are repeatedly and alternately switched automatically at definite time intervals with use of a timing device, thus making it possible to perform adsorption in one of the adsorbent beds, while desorption is taking place in other adsorbent bed(s). Efficiency of such system is much higher than that of the system using a single bed of adsorbent. Following desorption a dehydrating gas may be used to dry the adsorbent bed.

DESCRIPTION OF THE INVENTION

FIG. 2 shows the schematic diagram of an embodiment 10 of the present invention. Arterial blood from the patient is sent through tube or pipe 12 by blood pump 14 to any conventional hemodialyzer 16 containing any dialyzing fluid and is returned through pipe 18 to the vein. The recirculating dialysate from the hemodialyzer 16 is sent by pump 20 directly into one of the adsorbent beds 22a, 22b and is recycled through the recirculating dialysate tank 24 back to the hemodialyzer 16. The two adsorbent beds 22a, 22b are used for adsorption and desorption alternately. The valves 26 at the bottom and 28 at the top of the adsorbent beds may be three-way solenoid valves, or other suitable valves operated by a conventional timer 30.

To prevent the dialysate from being diluted, i.e. by water for desorption remaining in the adsorbent bed, desorption is first performed with water and then with fresh dialysate from the fresh dialysate tank 32. Either water for desorption from tank 34 or fresh dialysate for desorption from tank 32 is drawn by pump 36 through the valve 24 near the bottom of said tanks, and is sent to the top of one of the adsorbent beds 22a, 22b through valve 28. The waste fluid passes through line 38.

The following is an example of the experimental data obtained with the apparatus of FIG. 2.

A hollow fiber kidney (Cordis-Dow Model-4) was used as the hemodialyzer. 30 l of a simulated body fluid, i.e. a conventional dialysate solution in which urea and creatinine were dissolved, was used in lieu of blood. Its flow rate through the hemodialyzer was 250 ml per minute. The volume of the recirculating dialysate tank was 4 liters. The flow rate of the recirculating dialysate was 200 ml per minute. The flow rates of water and fresh dialysate used for desorption were both 200 ml per minute. Two beds of adsorbent, each containing 450 g of activated charcoal, were used alternately. The cycle time was 15 minutes for adsorption, 11 minutes for desorption with water, and 4 minutes for desorption with fresh dialysate. The cycle times or rates are not found to be critical.

FIG. 3 shows time-dependent decrease in the concentrations of urea and creatinine in the simulated body fluid in said experiment with the apparatus of FIG. 2. It also shows that the urea concentration in the recirculating dialysate stays at very low values throughout the dialysis.

FIG. 4 shows the schematic diagram of another embodiment of application of the present invention. Blood withdrawn from the artery of the patient enters through tube 12 into the hemodialyzer 16 and returns to the vein through tube 18. Any type of hemodialyzer 16, e.g. a Kiil-type shown in FIG. 4, can be used. 40 designates the dialyzing membrane. The dialysate in the recirculating dialysate tank 24 is recirculated by pump 20 through one of the adsorbent beds 22a, 22b and the hemodialyzer 16 and returns to the recirculating dialysate tank 24. 42 is the tube for the make-up dialysate. In the example shown in FIG. 4, the two adsorbent beds 22a, 22b are used alternately for repeated adsorption and desorption. Solenoid valves (or cocks) operated by a conventional automatic timing device (timer) 44 are used as inlet valves 46 for the dialysate 21, outlet valves 48 for the dialysate, inlet valves 50 for water for desorption and outlet valves 52 for water for desorption. Under the situation shown in FIG. 4, the inlet 46 and outlet valves 48 for the dialysate for the adsorbent bed 22a are open, and the inlet and outlet valves for water for the adsorbent bed 22a are closed. Thus, adsorption is taking place in the adsorbent bed 22a. On the other hand, desorption is taking place in the adsorbend bed 22b, since the inlet 46 and outlet 48 valves for the dialysate for the adsorbent bed 22b are closed, and the inlet and outlet valves 50 and 52 for water for the adsorbent bed 22b are open. Fresh water for desorption enters through pipe 54 and spent water is discarded through pipe 38. It is preferable to let the dialysate and water flow in opposite directions. In the arrangement shown in FIG. 4, the zone in which adsorption takes place moves upward through the bed, and hence the zone near the top of the bed may not be saturated at the end of the adsorption period. Thus, it is faster to perform desorption by passing water downward from the top than passing water upward. After a certain time interval, all of said valves are switched so that adsorption takes place in the adsorbent bed 22b and desorption takes place in the adsorbent bed 22a. Thus, the adsorbent bed 22a and the adsorbent bed 22b are used alternately and repeatedly for adsorption and desorption. In case three or more beds of adsorbent are used, one of the adsorbent beds is used in rotation for adsorption, while desorption is performed in other adsorbent bed(s).

In order to displace with water the dialysate remaining in the adsorbent bed at the beginning of a desorption period, it is preferable to delay closing of valve 46 and opening of valve 52 appropriately. Similarly, it is better to delay closing of valve 50 and opening of valve 48 appropriately to displace water remaining in the adsorbent bed at the beginning of a adsorption period. Even when this is done, recycling dialysate may be diluted to some extent due to mixing with water for desorption. Thus, it is often necessary to make up fresh dialysate through pipe 42, by monitoring the concentration of the recycling dialysate, for example, by measuring electric conductivity of the dialysate.

Table I compares the data for the apparatus of FIG. 4 using two adsorbent beds with those for the apparatus of Blaney et al. using a single adsorbent bed. Compared with the system of Blaney et al., the system of FIG. 4 requires smaller amounts of activated charcoal and dialysate and lower flow rate of the recycling dialysate and still can remove more urea per unit time. Our equilibrium data on the adsorption of urea by activated charcoal (FIG. 1), agree approximately with the data of Blaney et al.

Table I

|  | Blaney et al. | present invention |
| --- | --- | --- |
| number of adsorbent bed(s) | 1 | 2 |
| required volume of activated charcoal | 3000 c.c. | 400 c.c. × 2 |
| volume of recirculation dialysate tank | 50 l | 6 l |
| flow rate of dialysate | 2 l/min | 0.3 l/min |
| cycle time | 7.5 min | 10 min |
| amount of urea removed | 11 g/3.5 hr | 30 g/8 hr |

FIG. 5 shows the schematic diagram of another embodiment of the present invention in which the adsorbent is dried by air after desorption with water. Under the situation shown in FIG. 5, adsorption of toxins is being performed in the adsorbent bed 22a, desorption with water is being performed in the adsorbent bed 22b, and adsorbent is being dried by hot air in the adsorbent bed 22c. In FIG. 5, functions of the components numbered are the same as those in FIG. 4. Hot air, about at 90° C, (though the temperature is not critical) enters through pipe 56 (air compressor and an air-heater, not shown in the drawings, are used) and then through the solenoid valve 58 to the adsorbent bed 22 in which drying of adsorbent is performed. The moist air leaves the adsorbent bed through the solenoid valve 60 and pipe 62 and is discharged to atmosphere. The flow rate of air must be large enough to vaporize water adhering to the surface of adsorbent particles within a cycle time of about 15 minutes. Valves for air entering and leaving the adsorbent bed, 58 and 60, respectively, are operated automatically by the timer 64.

Three adsorbent beds are used in rotation for adsorption, desorption, and drying, an indicated by the following schedule. Each cycle time is, for example, 15 minutes.

| adsorbent bed | 22a | 22b | 22c |
|---|---|---|---|
| cycle 1 | adsorption | desorption | drying |
| cycle 2 | desorption | drying | adsorption |
| cycle 3 | drying | adsorption | desorption |
| cycle 4 | adsporption | desorption | drying |

In such a scheme of operation, desorption is performed only with water. There occurs no dilution of the dialysate with water. However, the dialysate remaining in the adsorbent bed at the end of the adsorption period is lost with water for desorption. Such excellent results with the system of the present invention, as shown in three examples, far exceed simple expectation that the amount of urea adsorbed will be proportional to the amount of adsorbent used. The reasons for the high efficiency of the systems of the present invention are as follows.

(1) When two beds of adsorbent are used alternately, optimum cycle times for adsorption and desorption can be chosen to make the amount of adsorbent minimum.

(2) If only one adsorbent bed were used, the capacity of the recirculating dialysate tank should be fairly large. Otherwise, the concentration of urea etc. in the recirculating dialysate would rise rapidly during the desorption period, during which period the recirculating dialysate bypasses the adsorbent bed. Consequently the efficiency of the hemodialyzer would drop rapidly due to decreased concentration difference across the dialyzing membrane. On the other hand, if a fairly large tank were used to avoid a large increase in the concentration of urea etc. in the recirculating dialysate, the amount of urea etc. adsorbed per unit mass of adsorbent would be low because of the equilibrium relationship such as shown in FIG. 1, and consequently a large amount of adsorbent would be required. Thus, a system with a single adsorbent bed cannot be operated efficiently. Whereas, in the system of the present invention in which two or more adsorbent beds are used alternately or in rotation, a large recycling dialysate tank is not required, and hence a dialysate solution containing urea etc. at a high concentration can be fed to the adsorbent bed, thus making the required amount of adsorbent small. The concentration of urea etc. in the recirculating dialysate entering the hemodialyzer is always very low, because the dialysate always comes from one of the adsorbent beds which is performing adsorption, while the other adsorbent bed(s) is performing desorption and/or drying. This results in a large concentration difference across the dialyzing membrane and hence high efficiency of the hemodialyzer.

It must be pointed out that the main factor which determines the capacity of the apparatus of the present invention is not the equilibrium relationship for adsorption of urea etc. on the adsorbent, as in the case of a batch dialysate treatment system using an adsorbent, but is the rate of adsorption of urea etc. on an adsorbent, which is fairly high.

The excellent performance of the system of the present invention described above cannot be anticipated from a mere aggregation of the known practice of using adsorbent in the treatment of dialysate for the hemodialyzer and the known industrial practice of automatic cyclic switching of absorption and desorption operations. The apparatus of the present invention are much simpler and much lower in cost of construction than the conventional apparatus for continuous dilution of the dialysate concentration using an expensive proportioning pump. The required total amount of dialysate, including fresh dialysate for make-up or for desorption, is approximately one tenth (1/10) of that with the conventional apparatus. The cost of adsorbent is negligible, since it can be used many times repeatedly. Various adsorbents may be used other than charcoal such as alumina and others.

I claim:

1. In an artificial kidney apparatus having a hemodialyzer for treating a recirculating dialyzing fluid, an adsorbent bed for receiving said dialyzing fluid for removal of contained toxins, and a desorbing fluid for desorbing said adsorbent bed of said toxins, the improvement comprising:
   a plurality of adsorbent beds for treating said dialyzing fluid,
   first flow control means for repeatedly and alternately selecting one and then another of said adsorbent beds for receiving said dialyzing fluid,
   second flow control means for repeatedly and alternately selecting one of said adsorbent beds for receiving water as a desorbing liquid after said adsorbent bed received said dialyzing fluid, whereby one of said adsorbent beds will repeatedly and alternately receive the dialyzing fluid to remove toxins therefrom and thereafter water as the desorbing fluid to desorb said toxins and reactivate the adsorbent bed while another of said adsorbent beds passes through a reverse cycle,
   third flow control means for repeatedly and alternately selecting one of said adsorbent beds for receiving fresh dialyzing fluid to displace said water remaining in said adsorbent bed and to effect further desorption of said toxins in said adsorbent bed after said adsorbent bed received said water as a desorbing liquid.

2. A method of treating recirculating dialyzing fluid in an artificial kidney apparatus comprising:
   providing a plurality of adsorbent beds for treating said recirculating dialyzing fluid,
   repeatedly and alternately passing recirculating dialyzing fluid through one of said beds to adsorb contained toxins in said recirculating dialyzing fluid and thereafter passing water as desorbing liquid through said bed to desorb said toxins and regenerate said adsorbent bed, while simultaneously adsorbing toxins from said recirculating dialyzing fluid in another adsorbent bed
   and following the step of passing water as desorbing liquid repeatedly and alternately through said bed the step of removing said water from said adsorbent bed prior to adsorption of toxins by said adsorbent bed by passing fresh dialysate through said adsorbent bed.

3. The method of claim 2 wherein two adsorbent beds are repeatedly alternated.

4. In the artificial kidney of claim 1 including:

timing means for operatively connected to said first, second and third flow control means for limiting the period of time of each said adsorbent bed to alternately and repeatedly receive said dialyzing fluid, then said desorbing fluid and thereafter said fresh dialyzing fluid.

5. The artificial kidney apparatus of claim 1 including means for discharging as waste said displaced water.

6. The method of claim 2 including discharging as waste said displaced water.

* * * * *